(12) United States Patent
Jackson et al.

(10) Patent No.: US 11,192,913 B2
(45) Date of Patent: Dec. 7, 2021

(54) C-GLYCOSIDE AMINE DERIVATIVES AND METHODS OF MAKING

(71) Applicant: The United States of America, as Represented by the Secretary of Agriculture, Washington, DC (US)

(72) Inventors: Michael A. Jackson, Morton, IL (US); Neil P. Price, Edelstein, IL (US)

(73) Assignee: The United States of America, as represented The Secretary of Agriculture, Washington, DC (US)

(*) Notice: Subject to any disclaimer, the term of this patent is extended or adjusted under 35 U.S.C. 154(b) by 0 days.

(21) Appl. No.: 17/140,415

(22) Filed: Jan. 4, 2021

(65) Prior Publication Data

US 2021/0214383 A1 Jul. 15, 2021

Related U.S. Application Data

(60) Provisional application No. 62/958,987, filed on Jan. 9, 2020.

(51) Int. Cl.
  *C07H 7/02* (2006.01)
  *C07H 1/00* (2006.01)

(52) U.S. Cl.
  CPC .......... *C07H 7/02* (2013.01); *C07H 1/00* (2013.01)

(58) Field of Classification Search
  None
  See application file for complete search history.

(56) References Cited

U.S. PATENT DOCUMENTS

| | | |
|---|---|---|
| 8,314,219 B1 | 11/2012 | Price |
| 2004/0048785 A1 | 3/2004 | Dalko et al. |
| 2008/0081905 A1 | 4/2008 | Price |
| 2008/0153760 A1 | 6/2008 | Leroy et al. |
| 2016/0317416 A1 | 11/2016 | L'Oreal |

FOREIGN PATENT DOCUMENTS

WO  WO-2010063953 A2  *  6/2010  .............. A61K 8/60

OTHER PUBLICATIONS

Lee, K. P. K., et al. "Antibacterial effect of fructose laurate synthesized by Candida antarctica B lipase-mediated transesterification", Journal of Microbiology and Biotechnology 2016, 26 (9), 1579-1585.
Neta N. S. et al., "Sugar ester surfactants: Enzymatic synthesis and applications in food industry", Crit. Rev. Food Sci. Nutr. 2015, 55 (5), 595-610.
Perinelli, D. R. et al., "Lactose oleate as new biocompatible surfactant for pharmaceutical applications", Eur J Pharm Biopharm 2018, 124, 55-62.
Plat, T. et al., "Syntheses and applications of sucrose-based esters", J. Surfactants Deterg. 2001, 4 (4), 415-421.
Staron, J. et al., "Lactose esters: Synthesis and biotechnological applications", Crit. Rev. Biotechnol. 2018, 38 (2), 245-258.
Wagh, A. et al., "Effect of lactose monolaurate on pathogenic and nonpathogenic bacteria", Appl. Environ. Microbiol. 2012, 78 (9), 3465.
Wilk, K. A. et al., "Preparation and properties of new lactose-based surfactants", J. Surfactants Deterg. 2001, 4 (2), 155-161.
Ye, R. et al., "Solvent-free lipase-catalyzed synthesis of technical-grade sugar esters and evaluation of their physicochemical and bioactive properties", Catalysts 2016, 6 (6), 78.
Zhang, X. et al., "Characterization of enzymatically prepared sugar medium-chain fatty acid monoesters", J. Sci. Food Agric. 2015, 95 (8), 1631-1637.
KR International Search Report, dated Apr. 22, 2021.

* cited by examiner

*Primary Examiner* — Traviss C McIntosh, III
(74) *Attorney, Agent, or Firm* — G. Byron Stover; John D. Fado; Ariel L. Atkinson

(57) ABSTRACT

Disclosed are C-glycoside amine derivatives of the formula:

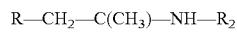

R—$CH_2$—C($CH_3$)—NH—$R_2$ wherein R is a saccharide (e.g., as described in U.S. Pat. No. 8,314,219) and $R_2$ is an acyl moiety derived from any ketone of the formula $R_3$—C(O)—$R_3$ wherein $R_3$ is C1 to C22 straight or branched chain hydrocarbon which may be saturated or unsaturated. In addition, a method for making the C-glycoside amine derivatives involving (1) reacting a saccharide (e.g., glucose) C-glycoside ketone with a catalyst (e.g., Rh), about 10 to about 25 fold excess $NH_3$, and an organic solvent (e.g., methanol) to form a saccharide C-glycoside amine, and (2) reacting said saccharide C-glycoside amine with a catalyst (e.g., Rh), an organic solvent (e.g., methanol), and an acyl moiety derived from any ketone of the formula $R_3$—C(O)—$R_3$ wherein $R_3$ is C1 to C22 straight or branched chain hydrocarbon which may be saturated or unsaturated to form said C-glycoside amine derivative.

4 Claims, 2 Drawing Sheets

Glucose          Pentane-2,4-dione          Glucose C-glycoside ketone

C-GLYCOSIDE AMINE DERIVATIVES AND METHODS OF MAKING

REFERENCE TO RELATED APPLICATION

This application claims the benefit of U.S. Provisional Application No. 62/958,987, filed 9 Jan. 2020, which is incorporated herein by reference in its entirety.

BACKGROUND OF THE INVENTION

Disclosed are C-glycoside amine derivatives of the formula:

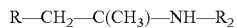

wherein R is a saccharide (e.g., as described in U.S. Pat. No. 8,314,219) and $R_2$ is an acyl moiety derived from any ketone of the formula $R_3$—C(O)—$R_3$ wherein $R_3$ is C1 to C22 straight or branched chain hydrocarbon which may be saturated or unsaturated. Also a composition containing at least one of the C-glycoside amine derivatives. In addition, a method for making the C-glycoside amine derivatives involving (1) reacting a saccharide (e.g., glucose) C-glycoside ketone with a catalyst (e.g., Rh), about 10 to about 25 fold excess $NH_3$, and an organic solvent (e.g., methanol) to form a saccharide C-glycoside amine, and (2) reacting said saccharide C-glycoside amine with a catalyst (e.g., Rh), an organic solvent (e.g., methanol), and an acyl moiety derived from any ketone of the formula $R_3$—C(O)—$R_3$ wherein $R_3$ is C1 to C22 straight or branched chain hydrocarbon which may be saturated or unsaturated to form said C-glycoside amine derivative.

There is a growing awareness of the need for biobased and sustainable chemicals. This is particularly true in the consumer products sector where demand for natural ingredients is growing. Within this trend rests the sugar-based surfactants that consist of a hydrophilic sugar head group (usually glucose, fructose, maltose, or sucrose) and an alkyl tail that contributes hydrophobicity. The alkyl tails often originate in triacylglycerides and range in carbon chain length from eight to 22 and can be saturated or unsaturated. With this general composition of a sugar and fatty acid, the compounds are seen as biodegradable, and these nonionic amphiphiles are commonly used as emulsifiers in foods, cosmetics, pharmaceuticals, and detergents. A review of sugar ester synthesis was written by Neta et al. (Neta, N. S., et al., Crit. Rev. Food Sci. Nutr., 55: 595-610 (2015)).

The carbohydrates of interest in the synthesis of surfactants are broadly available. Glucose is the most abundant monosaccharide and is produced by the enzymatic hydrolysis of starch. Maltose is a glucose dimer with an $\alpha(1\rightarrow 4)$ linkage and is prepared by the hydrolysis of starch by α-amylases producing maltose syrups that are up to 80 wt % maltose (Zhou, J., et al., Appl. Environ. Microbiol., 84: 1-12 (2018)). Maltose has uses in the pharmaceutical industry where it is used in tablet pressing and in food industries where it can enhance subtle flavors that may be overwhelmed by the sweetness of sucrose (Jeong, S. H., et al., J. Mater. Chem., 18: 3527-3535 (2008)). Lactose may be the more interesting carbohydrate to consider since it is a dairy waste product. The production of cheese results in a large volume of liquid whey. Whey is 5% lactose and is a waste product with high biological oxygen demand (BOD) that requires remediation (Das, B., et al., Process Saf. Environ. Prot., 101: 27-33 (2016); Carvalho, F., et al., Sci. Total Environ., 445-446, 385-396 (2013)). Cost effective utilization of the lactose stream has been of interest to the dairy industry for decades (Hobman, P. G., J. Dairy Sci., 67: 2630-2653 (1984); de Souza, R. R., et al., Chem. Eng. Process. Process Intensif., 49: 1137-1143 (2010)). There are few surfactants using lactose (Drummond, C. J., and D. Wells, Colloids Surf A Physicochem Eng Asp, 141: 131-142 (1998); Wilk, K. A., et al., J. Surfactants Deterg., 4: 155-161 (2001); Perinelli, D. R., et al., Eur J Pharm Biopharm, 124: 55-62 (2018)).

Herein we describe the synthesis and properties of a new series of surfactants prepared from β-C-glycoside amines and medium chain ketones, some of the latter of which may be prepared chemically from medium and long chain fatty acids. These compounds have potential as sustainable and environmentally benign emulsifiers. The sugar head groups, for example, can be derived from crop residues and dairy by-products. The hydrophobic tails, for example, can be synthesized by the ketonization of triacylglycerides from *Cuphea* sp. (Jackson et al. 2012) which is a promising new row crop for marginal lands in temperate regions.

SUMMARY OF THE INVENTION

Disclosed are C-glycoside amine derivatives of the formula:

wherein R is a saccharide (e.g., as described in U.S. Pat. No. 8,314,219) and $R_2$ is an acyl moiety derived from any ketone of the formula $R_3$—C(O)—$R_3$ wherein $R_3$ is C1 to C22 straight or branched chain hydrocarbon which may be saturated or unsaturated. Also a composition containing at least one of the C-glycoside amine derivatives. In addition, a method for making the C-glycoside amine derivatives involving (1) reacting a saccharide (e.g., glucose) C-glycoside ketone with a catalyst (e.g., Rh), about 10 to about 25 fold excess $NH_3$, and an organic solvent (e.g., methanol) to form a saccharide C-glycoside amine, and (2) reacting said saccharide C-glycoside amine with a catalyst (e.g., Rh), an organic solvent (e.g., methanol), and an acyl moiety derived from any ketone of the formula $R_3$—C(O)—$R_3$ wherein $R_3$ is C1 to C22 straight or branched chain hydrocarbon which may be saturated or unsaturated to form said C-glycoside amine derivative.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

Exemplary

Exemplary

DETAILED DESCRIPTION OF THE INVENTION

Disclosed are C-glycoside amine derivatives of the formula:

wherein R is a saccharide (e.g., as described in U.S. Pat. No. 8,314,219) and $R_2$ is an acyl moiety derived from any ketone of the formula $R_3$—C(O)—$R_3$ wherein $R_3$ is C1 to C22 straight or branched chain hydrocarbon which may be saturated or unsaturated. Also a composition containing at least one of the C-glycoside amine derivatives. In addition, a method for making the C-glycoside amine derivatives involving (1) reacting a saccharide (e.g., glucose) C-glycoside ketone with a catalyst (e.g., Rh), about 10 to about 25 fold excess $NH_3$, and an organic solvent (e.g., methanol) to form a saccharide C-glycoside amine, and (2) reacting said saccharide C-glycoside amine with a catalyst (e.g., Rh), an organic solvent (e.g., methanol), and an acyl moiety derived from any ketone of the formula $R_3$—C(O)—$R_3$ wherein $R_3$ is C1 to C22 straight or branched chain hydrocarbon which may be saturated or unsaturated to form said C-glycoside amine derivative.

Figure 1:
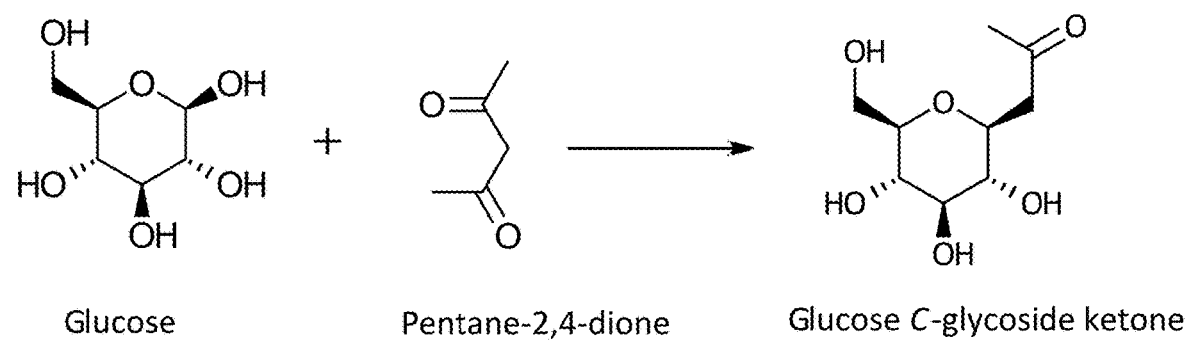
FIG. 1 is an example of a general reaction scheme showing the production of C-glycoside ketone from glucose and pentane-2,4-dione as described below; same chemistry applies to, for example, other saccharides such as galactose, xylose, maltose, and lactose.

The sugar head groups that we used in the preparation of the amphiphiles had 3-C-glycoside ketones as precursors (Lubineau, A., et al., Carbohydr. Res., 266: 211-219 (1995); Price, N. P. J., et al., J. Mass Spectrom., 43: 53-62 (2008)). These derivatives are prepared in high yield by the condensation of pentane-2,4-dione with, for example, an aldose in mildly alkaline aqueous solution (FIG. 1). Under thermodynamic control, high stereoselectivity toward the β anomer is achieved (Riemann, I., et al., Aust. J. Chem., 55: 147-154 (2002)). The appeal of these compounds as substrates is two-fold. First, the sugars are locked in the β-pyranose form, thus removing the complications sugars inject by their usual equilibrium mixture of linear, pyranose, and furanose forms. Second, the β-C-glycoside ketones are soluble in organic solvents (e.g., methanol), removing the challenges inherent to working with water, for example, its high boiling point. Sugars that are amenable to this chemistry include, for example, xylose, lyxose, ribose, arabinose, glucose, mannose, N-acetylglucosamine, cellobiose, maltose, lactose, galactose, allose, altrose, and polymers of these sugars.

One example of an aliphatic tail that can be attached to the glycoside head groups can originate from, for example, the seed oil of *Cuphea* sp. As described previously, *Cuphea* seed oil may be uniquely suited to the cross ketonization reaction with acetic acid (Jackson, M. A., et al., Appl. Catal., A Gen., 431-432, 157-163 (2012)). This condensation reaction converts two carboxylic acids to a ketone with the elimination of CO2 and water. For example, two acetic acid molecules react to form acetone. The fatty acid composition of *Cuphea* seed triacylglyceride is typically about 72% decanoic acid. In the ketonization reaction with acetic acid, the decanoic acid is converted to 2-undecanone at 90% yield. The aliphatic tail may also be any other C3-C22 ketone ranging from, for example, 2-pentanone to 2-nonadecanone and 10-nonadecanone.

General novel methods for the preparation of C-glycoside amines: A stirred reactor was charged with C-glycoside ketone (e.g., 5 g), hydrogenation catalyst (e.g., 500 mg 2 wt % Rh/C (rhodium on any support will work, in addition to platinum and palladium)), and an organic solvent such as alcohols like MeOH (e.g., 50 ml) or ethanol. The reactor was purged, for example, with hydrogen (or an inert gas like nitrogen or argon), to remove air prior to the addition of $NH_3$ (e.g., about 1.5 to about 3.1 bar (1.5-3.1 bar) anhydrous). The reactor was then heated to about 65° C. to about 100° C. (e.g., 65° to 100° C.) at which point it was charged to about 17 to about 70 bar (e.g., 17 to 70 bar) with H2. Reaction progress was monitored by MALDI-TOF (matrix-assisted laser desorption/ionization-time-of-flight) mass spectrometry. Upon completion (generally about 1 to about 6 h (e.g., 1-6 h)), the reactor was vented and allowed to cool. The catalyst was collected by filtration and the product collected from the filtrate by removal of the solvent under reduced pressure.

Figure 2:
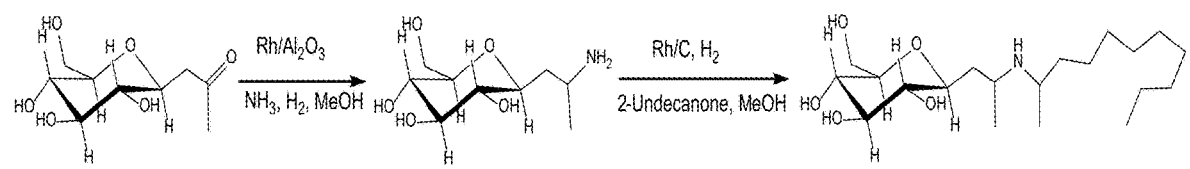
FIG. 2 is an example of a general reaction scheme showing the two-step conversion of glucose-C-glycoside ketone to glucose-C-glycoside 2-aminoundecane as described below. Both steps were carried out at 75° C. under 34 bar H2. The first reductive amination was carried out under 1.4 bar $NH_3$ while the second was performed with a 10 mol % excess of 2-undecanone.

The reductive amination of ketones or aldehydes with $NH_3$ generally leads to secondary amines since primary amines are more reactive than is $NH_3$ (Nakamura, Y., et al., ChemCatChem, 7: 921-924 (2015)). We surprisingly solved this potential problem by having about 10 to about 25 fold (e.g., 10-25 fold) molar excess (compared to the β-C-glycoside ketone) of $NH_3$ in the reactor. In fact, the reductive amination of the C-glycoside ketones of a saccharide (e.g., glucose, maltose, lactose) with $NH_3$ in an organic solvent (e.g., methanol) over catalyst (e.g., 2 wt % Rh/HMS) surprisingly proceeds readily in about 1 to about 6 h (e.g., 1-6 h) with little indication the amine reacts to form the secondary amine, or dimer product (FIG. 2).

General novel methods for the preparation of C-glycoside surfactants: The addition of the alkyl chain that imparts the amphiphilic qualities to the compounds was also accomplished through a reductive amination (RA). This second RA was between the C-glycoside amines and, for example, 2-undecanone (or other ketones as mentioned above). These reactions were performed in a solvent in which the C-glycosides are soluble (e.g., an organic solvent such as methanol, ethanol, or water), and were catalyzed by a hydrogenation catalyst (e.g., 5 wt % Rh/C (rhodium on any support will work, in addition to platinum and palladium)). As described for the first step above, the reactor was purged of air with hydrogen or an inert gas (nitrogen or argon) and then heated to about 65° to about 100° C. (e.g., 65° to 100° C.). The reactor was then charged to about 17 to about 70 bar (e.g., 17-70 bar) hydrogen and the reaction was complete in about 3 to about 18 h (e.g., 3-18 h). This approach surprisingly avoided the limitation of nonspecific regioselectivity that plagues chemical esterification of sugars with fatty acids (van Kempen, S. E. H. J., et al., Food Chem., 138: 1884-1891 (2013)). As described below, we prepared 2-aminoundecane derivatives of glucose, lactose, maltose, and maltotriose. Other possible ketone alkyl groups include, for example, 2-tridecanone, 2-pentadecanone, 2-heptadecanone, 10-nonadecanone, and 2-nonadecanone. The reductive amination reactions are performed using, for example, rhodium as the active metal. Effective supports include, for example, $Al_2O_3$, $HMS-SiO_2$, C, and the zeolites ZSM-5, beta, and mordenite.

The above methods do not utilize homogeneous catalysts (e.g., Raney nickel), acid chlorides, or harsh solvents required in known methods to prepare sugar esters (Wilk, K. A., et al., J. Surfactants Deterg, 4(2): 155-161 (2001); Drummond, C. J., and D. Wells, Coll. Surf. A: Physicochem. Eng. Asp., 141: 131-142. (1998)). Nor are long reaction times (e.g., about 48 to about 72 hours (48-72 hours)) needed such as in the reactions mediated by enzymes (Zhao, L, et al., Food Chem, 187: 370-377. (2015)).

Other compounds (e.g., surfactants known in the art) may be added to the composition provided they do not substantially interfere with the intended activity and efficacy of the composition; whether or not a compound interferes with activity and/or efficacy can be determined, for example, by the procedures utilized below.

"Optional" or "optionally" means that the subsequently described event or circumstance may or may not occur, and that the description includes instances in which said event or circumstance occurs and instances where it does not. For example, the phrase "optionally comprising a known surfactant" means that the composition may or may not contain a known surfactant and that this description includes compositions that contain and do not contain a known surfactant. Also, by example, the phrase "optionally adding a known surfactant" means that the method may or may not involve adding a known surfactant and that this description includes methods that involve and do not involve adding a known surfactant.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The compounds described herein or compositions described herein to be used will be at least an effective amount of the compound or diluted solution of the compound; for fumigation the compounds used may have to be pure form (not mixed or adulterated with any other substance or material). Generally the concentration of the compounds will be, but not limited to, about 0.025% to about 10% (e.g., 0.025 to 10%, for example in an aqueous solution), preferably about 0.5% to about 4% (e.g., 0.5 to 4%), more preferably about 1% to about 2% (e.g., 1 to 2%). The composition may or may not contain a control agent for insects, such as a biological control agent or an insecticide known in the art to kill insects. Other compounds (e.g., insect attractants or other insecticides known in the art) may be added to the composition provided they do not substantially interfere with the intended activity and efficacy of the composition; whether or not a compound interferes with activity and/or efficacy can be determined, for example, by the procedures utilized below.

The composition containing the compounds disclosed herein include optionally a carrier (e.g., agronomically or physiologically or pharmaceutically acceptable carrier). The carrier component can be a liquid or a solid material. The term "carrier" as used herein includes carrier materials such as those described below. As is known in the art, the vehicle or carrier to be used refers to a substrate such as a mineral oil, paraffin, silicon oil, water, membrane, sachets, disks, rope, vials, tubes, septa, resin, hollow fiber, microcapsule, cigarette filter, gel, fiber, natural and/or synthetic polymers, elastomers or the like. All of these substrates have been used to controlled release effective amount of a composition containing the compounds disclosed herein in general and are well known in the art. Suitable carriers are well-known in the art and are selected in accordance with the ultimate application of interest. Agronomically acceptable substances include aqueous solutions, glycols, alcohols, ketones, esters, hydrocarbons halogenated hydrocarbons, polyvinyl chloride; in addition, solid carriers such as clays, laminates, cellulosic and rubber matrices and synthetic polymer matrices, or the like.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount. For example, about 1.0 g means 0.9 g to 1.1 g and all values within that range, whether specifically stated or not.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Preparation of C-glycoside amines: A 300 ml Parr Instruments stirred reactor was charged with 5 g C-glycoside ketone (FIG. 1), 500 mg 2 wt % Rh/C, and 50 ml MeOH. The reactor was purged with hydrogen to remove air prior to the addition of 30 psi anhydrous $NH_3$. The reactor was then heated to 75° C. at which point it was charged to 500 psi with H2. Reaction progress was monitored by MALDI-TOF (matrix-assisted laser desorption/ionization-time-of-flight) mass spectrometry. Upon completion (generally about 1 to about 4 h), the reactor was vented and allowed to cool. The catalyst was collected by filtration and the product collected from the filtrate by removal of the solvent under reduced pressure.

As noted above, the reductive amination of ketones or aldehydes with $NH_3$ generally leads to secondary amines since primary amines are more reactive than is $NH_3$ (Nakamura, Y., et al., ChemCatChem, 7: 921-924 (2015)). This potential problem was surprisingly solved by having a 10-25 fold molar excess of $NH_3$ in the reactor. In fact, the reductive amination of the C-glycoside ketones of glucose, maltose, and lactose with $NH_3$ in methanol over 2 wt % Rh/HMS catalyst surprisingly proceeds readily with little indication the amine reacts to form the secondary amine, or dimer product (FIG. 2).

Preparation of C-glycoside surfactants: As noted above, the addition of the alkyl chain that imparts the amphiphilic qualities to the compounds was also accomplished through a reductive amination (RA). This second RA was between the C-glycoside amines and 2-undecanone. These reactions were performed in methanol and were catalyzed by 5 wt % Rh/C. As noted above, this approach surprisingly avoided the limitation of nonspecific regioselectivity that plagues chemical esterification of sugars with fatty acids (van Kempen, S. E. H. J., et al., Food Chem., 138: 1884-1891 (2013)). We prepared 2-aminoundecane derivatives of four saccharides (i.e., glucose, lactose, maltose, and maltotriose).

NMR and MALDI-TOF MS data on the ketones, amines, and 2-aminoundecanes:

Glucose C-glycoside ketone: 1H NMR (500 MHz, D2O) δ 3.80 (m, 1H), 3.60 (m, 1H), 3.70 (m, 1H), 3.40 (t, J=8.9 Hz, 1H), 3.30 (m, 2H), 3.1 (t, 1H), 2.95 (dd, J=3.2, J=16 Hz, 1H), 2.66 (dd, J=9.0, J=16 Hz, 1H) 2.20 (s, 3H). 13C NMR (125 MHz, D2O) δ 213, 79.5, 77.3, 75.3, 73.2, 69.9, 60.7, 45.7, 30.0. MALDI-TOF MS: m/z 243, [M+Na]+.

Glucose C-glycoside amine: 1H NMR (500 MHz, D2O acidified with D2SO4). δ 3.80 (m, 1H), 3.60 (m, 1H), 3.70 (m, 1H), 3.32 (m, 1H), 3.30 (m, 1H), 3.18 and 3.15 (t, J=6.8 Hz, 2H), 1.81 and 1.75 (m, J=2.2 Hz, 1H), 1.52 (m, J=2.2 Hz, 1H) 1.20 (dd, J=6 Hz, 0.6H), 1.1 (dd, J=6 Hz, 2.4H). 13C NMR (125 MHz, D2O acidified with D2SO4) δ 79.5, 77.8, 77.1, 73.7, 70.0, 61.12×, 44.5, 42.8, 39.7, 39.3, 22.3, 20.9, 20.1. MALDI-TOF MS: m/z 222, [M+H]+, 244, [M+Na]+.

Glucose C-glycoside 2-aminoundecane: 1H NMR (500 MHz, DMSO-d6) δ 3.63 (m, 1H), 3.39 (m, 1H), 3.09 (m, 1H), 3.02 (m, 1H), 2.84 (m, 1H), 1.43 (m, 2H), 1.24 (bs, 16H) 0.93 (m, 6H), 0.85 (t, J=7.3 Hz, 3H). 13C NMR (125 MHz, DMSO-d6) δ 80.8, 79.0, 75.0, 71.0, 62.02×, 32.0, 29.6, 25.7, 24.0, 22.8, 21.9, 21.4, 14.5. MALDI-TOF MS: m/z 376, [M+H]+.

Maltose C-glycoside ketone: 1H NMR (500 MHz, D2O). δ 5.33, 5.28 (d, J=3.9 Hz, 1H), 3.83, 3.79, 3.73, 3.72, 3.71, 3.70, 3.65, 3.55, 3.52, 3.48, 3.36 (overlapping m, 14H), 3.36 (t, J=9.5 Hz, 1.4H), 3.20 (t, J=9.5 Hz, 0.6H), 2.96, 2.94, 2.92, 2.87 (overlapping m, 1.4H), 2.66 (dd, J=9.3 Hz, 0.6H), 2.22 (s, 1.4H), 2.21 (s, 1.8H). 13C NMR (125 MHz D2O) δ 213.2, 212.9, 99.6, 99.5, 78.1, 77.7, 77.0, 76.8, 75.1, 73.0, 72.9, 72.9, 72.7, 72.6, 71.7, 71.6, 71.1, 70.2, 69.3, 60.8, 60.5, 45.6, 40.1, 29.9, 29.8. MALDI-TOF MS: m/z 405, [M+Na]+.

Maltose C-glycoside amine: 1H NMR (500 MHz, D2O). δ 5.33 (d, J=3.9 Hz, 1H), 3.78, 3.69, 3.67, 3.64, 3.54, 3.52, 3.46, 3.40, 3.39, 3.35 (overlapping m, 22H), 1.95 (m, 1H), 1.60 (m, 1H), 1.18 (2d, J=6.5 Hz, 2H). 13C NMR (125 MHz D2O) δ 99.6, 77.9, 77.7, 77.6, 77.1, 77.0, 73.5, 72.9, 72.7, 72.7, 71.7, 71.7, 69.3, 60.9, 60.9, 60.7, 60.5, 60.5, 48.9, 45.8, 37.3, 19.4. MALDI-TOF MS: m/z 384, [M+H]+, 406, [M+Na]+.

Maltose C-glycoside 2-aminoundecane: 1H NMR (500 MHz, D2O acidified). 5.34, 5.29 (2 unresolved doublets, 1H), 3.85, 3.76, 3.66, 3.65, 3.64, 3.53, 3.52 (m, 14H), 3.36, 3.34 (m, 2.1H), 3.17 (m, 0.6H), 1.60 (bs, 1H), 1.42 (bs, 1H), 1.27, 1.23, 1.18, 1.15 (bm, 19H), 0.74 (t, J=6.7 Hz, 3H). 13C NMR (125 MHz D2O) δ 99.6, 99.1, 77.9, 77.8, 77.5, 73.0, 72.8, 72.7, 71.6, 71.5, 69.2, 60.9, 60.5, 51.9, 49.6, 32.5, 31.2, 22.1, 16.3, 15.8, 15.3, 13.4. MALDI-TOF MS: m/z 538, [M+H]+, 560, [M+Na]+.

Lactose C-glycoside ketone: 1H NMR (500 MHz, D2O). δ 4.50 (m, 0.4H), 4.38, 4.37 (d, J=7.8 Hz, 1H together. These integrate 2:1), 3.87 (dd, J=3.3), 3.83, 3.74, 3.73, 3.71, 3.70, 3.66, 3.60, 3.57, 3.49, 3.48 (unresolved group, 13H), 3.22 (m, 0.6H), 2.96 (dd, J=2.8 Hz, J=16.8 Hz, 0.6H), 2.90 (m, 0.4H), 2.22, 2.21 (2 singlets, 3H). 13C NMR (125 MHz D2O) δ 102.9, 78.7, 78.5, 78.3, 75.8, 75.4, 75.1, 72.8, 72.5, 72.3, 71.7, 71.6, 71.0, 70.1, 68.6, 61.0, 60.1, 45.6, 39.7, 29.8. MALDI-TOF MS: m/z 405, [M+Na]+.

Lactose C-glycoside amine: 1H NMR (500 MHz, D2O). δ 4.36, (d J=7.8 Hz, 1H), 3.87, 3.85, 3.70, 3.64, 3.58, 3.55, 3.53, 3.47, 3.45, 3.44 (overlapping m, 15H), 3.19 (ddd, J=3.1, J=9, J=20 Hz, 1H), 1.97 (m, 1H), 1.66 (m, 1H), 1.21 (d, J=6.7 Hz, 3H). 13C NMR (125 MHz D2O) δ 102.9, 78.6, 78.5, 78.3, 78.1, 77.4, 75.8, 75.7, 73.2, 72.9, 72.5, 71.0, 68.6, 61.0, 60.3, 60.2, 48.9, 46.2, 44.4, 36.6, 36.5, 19.4, 18.9. MALDI-TOF MS: m/z 384, [M+H]+, 406, [M+Na]+.

Lactose C-glycoside 2-aminoundecane: 1H NMR (500 MHz, D2O, acidified). δ 4.31 (dt, J=7.8 Hz, 1H), 3.84, 3.81, 3.65, 3.61, 3.60, 3.54, 3.50, 3.46, 3.42, 3.29, 3.17 (m, 17H), 2.1-1.7 (m, 2H), 1.59 (m, 1H), 1.42, 1.27 (t, J=5.7 Hz, 3H), 1.16 (m, 15H), 0.74 (t, J=7.1 Hz, 3H). 13C NMR (125 MHz D2O) δ 102.9, 102.8, 78.6, 78.5, 78.4, 78.2, 78.0, 75.6, 75.3, 73.1, 72.9, 72.5, 70.9, 68.5, 61.0, 60.3, 51.9, 49.5, 32.6, 31.2, 28.6, 28.5, 28.4, 28.3, 22.0, 16.2, 15.8, 15.6, 15.3, 13.4. MALDI-TOF MS: m/z 538, [M+H]+, 560, [M+Na]+.

Critical micelle concentrations (CMC) of the surfactants prepared from glucose, maltose, and lactose, and 2-undecanone are between 0.1 to 5.5 mM. The CMC is an important trait of surfactants. When amphiphiles are placed in water at concentrations near the CMC, they aggregate such that the polar head group forms an exterior surface that orients the alkyl tails in an interior core. This core has properties similar to organic solvents. At concentrations above the CMC, characterizations of the bulk solution change; for example, the surface tension is lowered, the solution wets surfaces better, and water-insoluble materials dissolve in the core of the micelles. Therefore, the CMC serves to guide utility of a surfactant in detergents, cosmetics, wetting agents, or food uses.

When surfactants are used in detergent formulations, antibiotic activity is an important trait. The antibiotic activity of the surfactants prepared from the saccharides glucose, maltose, and lactose, and 2-undecanone were measured against several microorganisms of interest in the food, human health, and agricultural areas. The concentrations at which these compounds inhibited growth of the organisms, that is, the microbial inhibition concentration (MIC) were surprisingly as low as 0.31 mM. These can be compared to values known for sugar fatty acid esters such as those of Zhao et al. (Zhao, L., et al., Food Chem., 187: 370-377 (2015)) who reported a MIC for sucrose caprate of 2.5 mM against *Bacillus subtilis* and 10 mM against *Escherichia coli*. Staron et al. reported a MIC of 5.9 mM against *B. cereus* for dodecanoyl lactose (Staroń, J., et al., Crit. Rev.

Biotechnol., 38: 245-258 (2018)). Galactose laurate has a MIC of 0.14 mM against *Streptococcus mutans* (Watanabe, T., et al., Curr. Microbiol., 41: 210-213 (2000)). The CMC values for the β-C-glycoside 2-aminoundecanes were 0.1-5.5 mM. The 3-C-glycoside 2-aminoundecanes surprisingly had antimicrobial activity against *Bacillus subtilis, Pseudomonas aeruginosa, Envinia amylovora, Escherichia coli*, and *Mycobacterium smegmatis* with the glucose derivative having the greatest activity with a minimum inhibitory concentration of 0.31 mM and a minimum bactericide concentration of 0.62 mM against all gram positive organisms tested. Against the gram negative *Enwiinia* and *Escherichia* the MIC was surprisingly 0.62 mM.

Summary: β-C-glycoside ketone derivatives of saccharides glucose, lactose, and maltose were converted to amines via a reductive amination using 2 wt % Rh/HMS (Rh/C or Rh/Al$_2$O$_3$ can be used) in ammoniacal methanol under about 500 psi H2 (pressure can be about 350 psi). The amines were isolated and then these molecules were used as the amine in the reductive amination of 2-undecanone prepared from the seed oil of *Cuphea*. The resulting β-C-glycoside 2-aminoundecanes were characterized by MALDI-TOF mass spectrometry, 2D nmr, and CHN analyses. The detergency of the products was measured by fluorescence detection to measure the critical micelle concentration. The CMC values for the β-C-glycoside 2-aminoundecanes were surprisingly in the range of 0.1 mM to 5.5 mM. The β-C-glycoside 2-aminoundecanes surprisingly had antimicrobial activity against *Bacillus subtilis, Pseudomonas aeruginosa, Envinia amylovora, Escherichia coli*, and *Mycobacterium smegmatis* with the glucose derivative having the greatest activity with a minimum inhibitory concentration of 0.31 mM and a minimum bactericide concentration of 0.62 mM against all gram positive organisms tested. Against the gram negative *Erwiinia* and *Escherichia* the MIC was 0.62 mM.

All of the references cited herein, including U.S. Patents and U.S. Patent Application Publications, are incorporated by reference in their entirety. Also incorporated by reference in their entirety are the following references: U.S. Pat. Nos. 8,314,219; 8,541,626.

Thus, in view of the above, there is described (in part) the following:

A C-glycoside amine derivative of the formula:

R—CH$_2$—C(CH$_3$)—NH—R$_2$ wherein R is a saccharide (e.g., as described in U.S. Pat. No. 8,314,219) and R$_2$ is an acyl moiety derived from any ketone of the formula R$_3$—C(O)—R$_3$ wherein R$_3$ is C1 to C22 straight or branched chain hydrocarbon which may be saturated or unsaturated.

A composition comprising (or consisting essentially of or consisting of) at least one C-glycoside amine derivative of the formula:

R—CH$_2$—C(CH$_3$)—NH—R$_2$ wherein R is a saccharide (e.g., as described in U.S. Pat. No. 8,314,219) and R$_2$ is an acyl moiety derived from any ketone of the formula R$_3$—C(O)—R$_3$ wherein R$_3$ is C1 to C22 straight or branched chain hydrocarbon which may be saturated or unsaturated; and optionally a carrier.

A method of making a C-glycoside amine derivative of the formula:

R—CH$_2$—C(CH$_3$)—NH—R$_2$ wherein R is a saccharide (e.g., as described in U.S. Pat. No. 8,314,219) and R$_2$ is an acyl moiety derived from any ketone of the formula R$_3$—C(O)—R$_3$ wherein R$_3$ is C1 to C22 straight or branched chain hydrocarbon which may be saturated or unsaturated; said method comprising (or consisting essentially of or consisting of) (1) reacting a saccharide (e.g., glucose) C-glycoside ketone with a catalyst (e.g., Rh), about 10 to about 25 fold excess NH$_3$, and an organic solvent (e.g., methanol) to form a saccharide C-glycoside amine, and (2) reacting said saccharide C-glycoside amine with a catalyst (e.g., Rh), an organic solvent (e.g., methanol), and an acyl moiety derived from any ketone of the formula R$_3$—C(O)—R$_3$ wherein R$_3$ is C1 to C22 straight or branched chain hydrocarbon which may be saturated or unsaturated to form said C-glycoside amine derivative.

The above method, wherein the method does not utilize homogeneous catalysts (e.g., Raney nickel).

The above method, wherein the method does not utilize acid chlorides.

The above method, wherein the method does not utilize harsh solvents required in known methods to prepare sugar esters.

The above method, wherein the method does not utilize long reaction times (e.g., about 48 to about 72 hours).

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element (e.g., method (or process) steps or composition components) which is not specifically disclosed herein. Thus, the specification includes disclosure by silence ("Negative Limitations In Patent Claims," AIPLA Quarterly Journal, Tom Brody, 41(1): 46-47 (2013): " . . . Written support for a negative limitation may also be argued through the absence of the excluded element in the specification, known as disclosure by silence . . . Silence in the specification may be used to establish written description support for a negative limitation. As an example, in *Ex parte Lin* [No. 2009-0486, at 2, 6 (B.P.A.I. May 7, 2009)] the negative limitation was added by amendment . . . In other words, the inventor argued an example that passively complied with the requirements of the negative limitation . . . was sufficient to provide support . . . This case shows that written description support for a negative limitation can be found by one or more disclosures of an embodiment that obeys what is required by the negative limitation . . . ."

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A C-glycoside amine derivative of the formula:

R—CH$_2$—C(CH$_3$)—NH—R$_2$ wherein R is a saccharide and R$_2$ is an alkyl moiety derived from any ketone of the formula R$_3$—C(O)—R$_3$ wherein R$_3$ is C1 to C22 straight or branched chain hydrocarbon which may be saturated or unsaturated; wherein said saccharide is selected from the group consisting of glucose, lactose, maltose, and maltotriose.

2. A composition comprising at least one C-glycoside amine derivative of the formula:

R—CH$_2$—C(CH$_3$)—NH—R$_2$ wherein R is a saccharide and R$_2$ is an alkyl moiety derived from any ketone of the formula R$_3$—C(O)—R$_3$ wherein R$_3$ is C1 to C22 straight or branched chain hydrocarbon which may be saturated or unsaturated; and optionally a carrier; wherein said saccharide is selected from the group consisting of glucose, lactose, maltose, and maltotriose.

3. A method of making a C-glycoside amine derivative of the formula:

R—CH$_2$—C(CH$_3$)—NH—R$_2$ wherein R is a saccharide and R$_2$ is an alkyl moiety derived from any ketone of the formula R$_3$—C(O)—R$_3$ wherein R$_3$ is C1 to C22 straight or branched chain hydrocarbon which may be saturated or unsaturated; said method comprising (1) reacting a saccharide C-glycoside ketone with a catalyst, about 10 to about 25 fold excess NH$_3$, and an organic solvent to form a saccharide C-glycoside amine, and (2) reacting said saccharide C-glycoside amine with a catalyst, an organic solvent, and an alkyl moiety derived from any ketone of the formula R$_3$—C(O)—R$_3$ wherein R$_3$ is C1 to C22 straight or branched chain hydrocarbon which may be saturated or unsaturated to form said C-glycoside amine derivative.

4. The method according to claim 3, wherein said saccharide is selected from the group consisting of glucose, lactose, maltose, and maltotriose.

* * * * *